United States Patent [19]

Cahalan et al.

[11] Patent Number: 4,581,821
[45] Date of Patent: Apr. 15, 1986

[54] METHOD OF PREPARING TAPE ELECTRODE

[75] Inventors: Patrick T. Cahalan, Champlin; Arthur J. Coury, St. Paul, both of Minn.

[73] Assignee: Medtronic, Inc., Minneapolis, Minn.

[21] Appl. No.: 457,670

[22] Filed: Jan. 13, 1983

Related U.S. Application Data

[60] Division of Ser. No. 121,387, Feb. 14, 1980, Pat. No. 4,391,278, which is a continuation-in-part of Ser. No. 968,489, Dec. 11, 1978, abandoned.

[51] Int. Cl.$^4$ .............................................. H01R 43/02
[52] U.S. Cl. ........................................ 29/877; 429/217
[58] Field of Search ....................... 429/217; 128/641; 29/623.5, 884, 877

[56] References Cited

U.S. PATENT DOCUMENTS

| | | | |
|---|---|---|---|
| 3,972,329 | 8/1976 | Kaufman | 128/641 |
| 3,993,049 | 11/1976 | Kater | 128/641 X |
| 4,063,352 | 12/1977 | Bevilacqua | 29/884 |
| 4,066,078 | 1/1978 | Berg | 128/641 |
| 4,125,110 | 11/1978 | Hymes | 128/641 |
| 4,195,121 | 3/1980 | Peterson | 264/104 X |
| 4,245,016 | 1/1981 | Rampel | 429/217 X |

Primary Examiner—Howard N. Goldberg
Assistant Examiner—Carl J. Arbes
Attorney, Agent, or Firm—Vidas & Arrett

[57] ABSTRACT

A method of preparing an improved medical electrode particularly adaptable to tape-like configurations for use in sensing and stimulation applications in which the electrode is applied to the skin. An essential electrode component comprises a mixture of a polymerized form of 2-acrylamido-2-methylpropanesulfonic acid or one of its salts with water and/or an alcohol. The mixture possesses electrically conductive properties, flexible properties and adhesive properties particularly lending itself to skin contact and adhesion.

16 Claims, 3 Drawing Figures

METHOD OF PREPARING TAPE ELECTRODE

This is a division of application Ser. No. 121,387, filed Feb. 14, 1980 now U.S. Pat. No. 4,391,278 issued July 3, 1983 which was a continuation-in-part of U.S. patent application Ser. No. 968,489, filed Dec. 11, 1978 and entitled TAPE ELECTRODE (now abandoned).

DESCRIPTION

1. Background of Prior Art

In its preferred embodiments this invention is directed to the preparation of medical electrodes for application to the skin. Skin electrodes are of varying types and may be used either as transmission electrodes or as sensing i.e., monitoring electrodes. A wide variety of design configurations have been provided in the past for these kinds of electrodes, all of which are applicable to this invention.

A desirable skin electrode is one which maintains good electrical contact with the skin and is free of localized current "hot spots" i.e., exhibits uniform conductivity. For example, a prior art electrode utilizing karaya gum tends to creep in use and flatten out, exposing the skin to possible direct contact with the current distribution member or lead wire.

It is an object of this invention to prepare electrodes in which the component contacting the skin possesses superior adhesive properties and uniform electrical characteristics. The adhesive properties are able to resist appreciable skin moisture, allowing the electrodes to be used for several days at a time. It is also substantially homogeneous and creep resistant and is thus able to avoid the development of "hot spots". The skin contacting component is also inherently electrically conductive, not requiring electrically conductive additives.

It is further an object of this invention to prepare electrodes having desirable elastic properties.

2. Brief Summary of Invention

The electrodes prepare by this invention essentially comprise electrical lead means contacting a mixture of polymerized 2-acrylamido-2-methylpropanesulfonic acid or one of its salts with water and/or an alcohol formed into a tacky conductive body. Polymer mixtures and copolymers may also be used as described below in detail. The mixture gels and takes the form of a self-supporting flexible material having adhesive properties. Additionally, it has inherent electrically conductive properties. Other constituents may optionally be included in the mixture and various components such as backing supports, differing electrical lead arrangements, current distributors and so forth may be used.

DETAILED DESCRIPTION OF THE INVENTION

Figure 1:
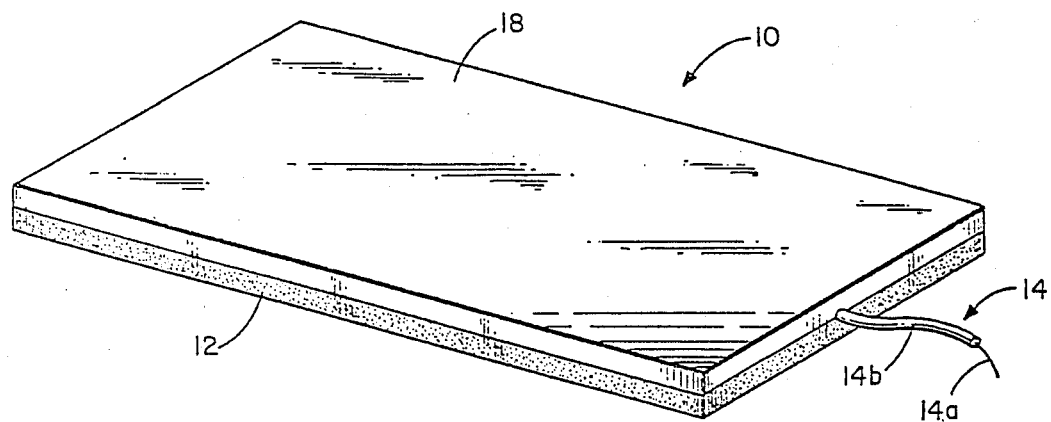
FIG. 1 is a schematic perspective view of an electrode according to the invention.
Figure 2:
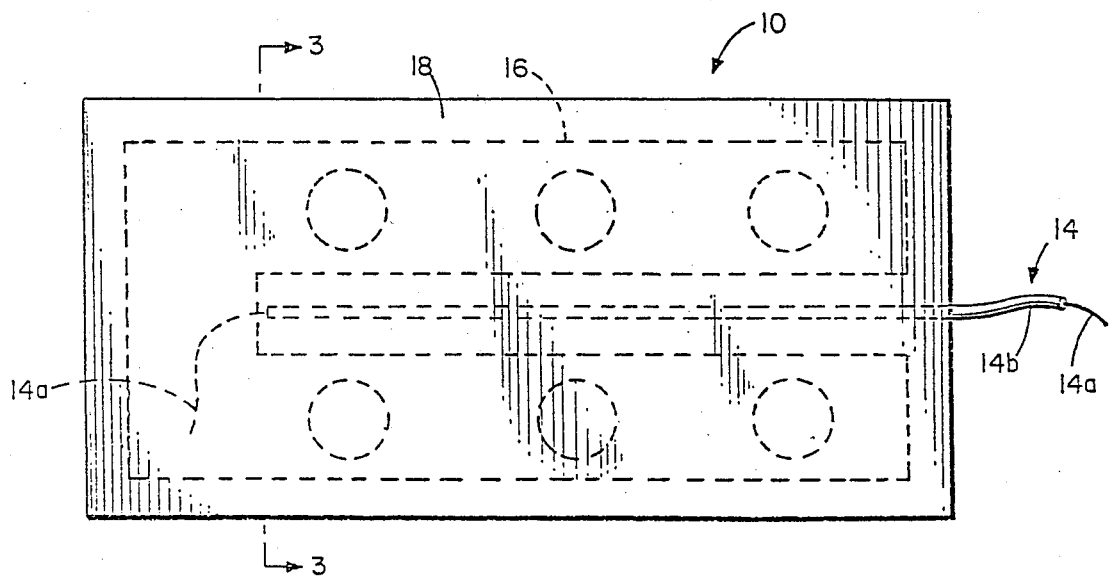
FIG. 2 is an elevational view of the electrode of FIG. 1.
Figure 3:
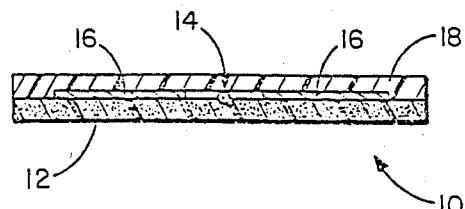
FIG. 3 is a cross-sectional view taken along line 3—3 of FIG. 2.

As previously pointed out, this invention particularly lends itself to preparation of medical electrodes of varying types, shapes and configurations. For exemplary purposes herein, a skin electrode 10 is shown in one of the common rectangular configurations.

Electrode 10 includes flexible, adhesive and conductive member 12 for contacting the skin. An electrical lead means 14, including a conductive member 14a and an insulating sheath or covering 4b, electrically contacts member 12.

In its most preferred form, as shown in the Figures, the electrode also includes an electrical current distribution member 16 which also electrically contacts electrical conductor 14a and member 12. Member 12 is referred to herein as a substrate. Current distribution member 16 is preferably formed of a metallic foil, such as stainless steel foil, which is readily available in very thin configuration or form such as 0.001 inches. Such a foil may be included in the electrode without having any substantial effect on its flexibility. Due to the adhesive nature of the substrate 12, the foil readily adheres thereto. A separate adhesive such as is described below may be used for this purpose and in some instances may be desired. Other forms of distribution member 16 may be used, such as wire mesh, conductive cloth or the like.

The preferred embodiment of the electrode as shown in the Figures also includes a support or backing 18, the chief purpose of which is to provide a protective and supportive member for the substrate. A preferred backing material is polyethylene foam. One such material is commercially available from Fasson, Inc., a division of Avery International of Paynesville, Ohio, under the trade designation MED 416. The material is a four pound density cross-linked polyethylene foam coated with a tacky adhesive material of an acrylic type. The foam is 1/16th of an inch thick. However, various thicknesses may be used. The foam need not be coated with the adhesive since it will in most instances, readily adhere to substrate 12 which, as previously pointed out, is adhesive itself.

The preferred embodiment makes use of the adhesive coated foam as backing 18, the stainless steel foil current distribution member 16 and substrate member 12. The substrate member may be of various thicknesses, about 0.025 to 0.250 inches being preferred. Greater thicknesses may be used as dimension is not critical as long as the electrical resistance is not excessive for the particular use involved.

In operation and use, electrode 10 is applied with conductive substrate 12 in direct contact with the skin. The adhesive properties of substrate 12 eliminate the need for separate adhesive tape or any other separate securing measures to hold electrode 10 in continuous contact with the skin. Upon prolonged exposure or use, the substrate may be wiped with water or alcohol to increase its adhesiveness. Electrical signals either to or from the skin, depending on the type of electrode application desired, are conducted through substrate member 12, the current distribution member 16 and electrical lead means 14 including wire 14a. Preferably, wire 14a contacts distribution member 16 by being held between it and backing 18.

In a transmission type of arrangement, lead 14 receives electrical signals from an external apparatus (not shown). These signals are conducted into the current distribution member 16 which in turn conducts them into the conductive substrate 12. In this manner current densities are uniformly distributed over the area of substrate 12 and in turn uniformly transmitted to the skin surface in contact with substrate 12. In a sensing or monitoring arrangement, the flow of electricity is reversed in direction, originating at the skin and being conducted through the substrate 12, distribution member 16, lead wire 14a and to a suitable electro-medical monitoring apparatus (not shown).

The composition of conductive member 12 is unique to the invention. As previously stated, it includes polymerized 2-acrylamido-2-methylpropanesulfonic acid or a soluble salt thereof mixed with water and/or an alcohol, preferably glycerol or propylene glycol, in flexible sheet-like form. Copolymers of it may also be used and it may be blended with additional polymeric thickneners and the like. Other non-volatile alcohols, eg., sorbitol may be used too. The components are provided in such relative amounts as to form a flexible, self-supporting material with substantial shape retention, which has adhesive properties, and which is electrically conductive.

The 2-acrylamido-2-methylpropanesulfonic acid or its soluble salt may be incorporated into the mixture in the monomer form and then polymerized to form the substrate body. Alternatively, the polymerized acid or its soluble polymerized salt may be incorporated into the mixture directly following which the substrate body is formed. Both approaches are illustrated in the examples below.

In the principal preferred embodiments, substrate member 12 comprises a sheet of polymerized material formed from 2-acrylamido-2-methylpropanesulfonic acid monomer purchased from The Lubrizol Corporation and sold under the tradename AMPS, a registered trademark. The monomer upon being dissolved in water, is polymerized to attain a shape-retaining, sheet-like form which is flexible, conductive and adhesive. It is preferred that the monomer be "refined" grade as per the Lubrizol "Process For The Manufacture of Refined AMPS" dated Dec. 14, 1976. Briefly, refined monomer is made by dissolving reaction grade monomer in methanol and recrystallizing it. Examples 1-9 are of this type.

The term "polymer" as used hereinbelow refers to polymers of 2-acrylamido-2-methylpropanesulfonic acid or its soluble salts and, where appropriate, it is further characteristized by "acid" or "salt" for additional specificity. The term "monomer" herein refers to the monomeric form of these compounds.

EXAMPLE 1

50 g. of the commercially available acid monomer were dissolved in 50 g. of distilled water. The mixture was purged with nitrogen for about 10 minutes before adding the initiators. Initiator was added. The Lubrizol Corp. recommends ferrous sulfate and hydrogen peroxide in small amounts eg., 0.01 g. ferrous sulfate heptahydrate and 0.25 g. hydrogen peroxide in a 0.05% solution, which was used in this example. Upon addition of the initiator, the mixture was poured into a tray in an enclosed nitrogen atmosphere to form a rectangular sheet having a thickness of about 0.125 inches. 0.25 inch thick sheets have also been prepared in this way. After pouring, the mixture rapidly gelled to a flexible material with adhesive conductive qualities.

EXAMPLE 2

25 g. of the acid monomer were dissolved in 25 ml. of deionized water. 4.24 g. of ammonium hydroxide were then dissolved in this mixture. The solution was purged with nitrogen for about 10 minutes and polymerization initiator was then added. The initiator was 1 ml. of a 0.38 g./100 ml. solution of potassium bisulfite, 1 ml. of a 0.38 g./100 ml. solution of potassium persulfate and 1 ml. of a 0.24 g./100 ml. solution of ferrous sulfate heptahydrate. 15 seconds were allowed for mixing then the mixture was poured into a mold under a nitrogen atmosphere to form the sheet material. The mixture rapidly gelled as in Example 1.

EXAMPLE 3

Same as Example 2 except 4.50 g. of lithium carbonate were substituted for the ammonium hydroxide. The resistance of the sheet was 7.5 kilo ohms for a sheet sample $1.5 \times 1 \times 0.125$ inches.

EXAMPLE 4

Same as Example 2 except 8.36 g. of potassium carbonate were substituted for the ammonium hydroxide. The resistance of the sheet was 2.1 kilo ohms for a sheet sample $1.5 \times 1 \times 0.125$ inches.

EXAMPLE 5

Same as Example 2 except 10.16 g. of sodium bicarbonate were substituted for the ammonium hydroxide. The resistance of the sheet was 2.1 kilo ohms for a sheet sample $1.5 \times 1 \times 0.125$ inches.

EXAMPLE 6

Another example of polymerizing the monomer and forming the sheet simultaneously was provided by mixing 50 g. of the monomer with 35 ml. of distilled water and 15 ml. of glycerol. The primary purpose of the addition of an alcohol such as glycerol is to retard drying of the polymerized sheet. The mixture was purged with nitrogen by bubbling about 10 minutes to substantially remove oxygen. Initiator in the form of 1 ml. of a 0.15% hydrogen peroxide solution was added. The mixture was then poured onto release paper (a silicone coated paper) under a nitrogen atmosphere and it very quickly gelled to be self-supporting. It was then placed in an oven at 50° C. for two hours to remove surface moisture. When placed in the oven overnight at 50° C., the material lost substantial tackiness. However, the surface of the material which was against the release paper retained good adhesive properties.

EXAMPLE 7

The same procedure was used as in Example 6 except that 10 ml. of glycerol and 40 ml. of water were used. The resulting sheet was more firm than that of Example 6.

EXAMPLE 8

Another sheet electrode was prepared as in Example 1. After polymerization, the electrode surface was wiped with glycerol and left exposed to ambient environment. Wiping was found to retard drying for at least 7 days. However, storage in sealed plastic bags was also found to be effective in preventing drying of the polymer sheet.

EXAMPLE 9

Eight sheet-like pads of polymerized material were prepared as in Example 1 except the initiator used was: 1 ml. of a 0.38 g./100 ml. solution of potassium bisulfite, 1 ml. of a 0.38 g./100 ml. solution of potassium persulfate and 1 ml. of a 0.24 g./100 ml. solution of ferrous sulfate heptahydrate. Each pad was about $4.5 \times 7 \times 0.125$ inches in size. They were tested for skin irritation on both laboratory animals and humans with no primary skin irritation resulting.

The typical electrical resistivity of the polymerized sheet prepared and described in Examples 1 and 6–9 was about $3 \times 10^2$ ohm-cm. and the sheet was substantially colorless and substantially transparent in appearance.

The monomer and its salts may be polymerized in aqueous solutions by common water soluble radical initiators or redox systems. It can also be polymerized in emulsion, rather than in solution, using common vinyl polymerization techniques. The molecular weight of the polymer may be varied by changing the initiator concentration, the monomer concentration, the temperature or by the use of a chain transfer agent such as a mercaptan.

The molecular weight of the polymer formed for use herein is not critical so long as it is high enough to form a self-supporting material, believed to be more accurately characterized as a gel. The higher the molecular weight, the easier the material is to handle and the better its performance, such as resistance to creep and dehydration.

Since the polymer itself i.e., poly-2-acrylamido-2-methylpropanesulfonic acid and many of its polymerized salts are water soluble, the substrate member may also be prepared by dissolving already formed polymer in water or other suitable solvents such as alcohols and forming a sheet or film of desired thickness by compression forming or by solution casting and evaporating.

Additional constituents may be mixed with the polymer in such preparations also. Examples of such mixtures or "blends" are included below. Sheets of each were prepared and tested. The mixtures, in the amounts indicated below, were stirred together, placed between two pieces of Mylar, a registered trademark of E. I. Du Pont de Nemours, pressed to desired thickness, ranging from about 0.015 to about 0.25 inches for example, to form sheet or film, and dried overnight in an oven at 50° C.

EXAMPLE 10

Xanthan gum (as additional thickener): 4.8 g.
acid polymer: 0.2 g.
water: 1.0 g.
glycerol: 7.0 g.
flexibility—good, adhesion—good, residue—marginal, elasticity—acceptable, compression—excellent.

For purposes of definition herein, "residue" means tacky material left on skin after removal of the electrode and "compression" means resistance to flow with pressure.

EXAMPLE 11

Karaya gum (as additional thickener): 2.4 g.
acid polymer: 0.1 g.
glycerol: 3.5 g.
water: 0.5 g.
flexibility—excellent, adhesion—very good, residue—very good, elasticity—excellent, compresion—excellent.

EXAMPLE 12

Polyacrylamide-grafted corn starch (as additional thickener): 2.4 g.
acid polymer: 0.1 g.
glycerol: 3.5 g.
water: 0.5 g.
adhesion—excellent, compression—excellent. Resistivity $1.56 \times 10^4$ ohm-cm.

EXAMPLE 13

Hydroxypropyl Guar (as additional thickener): 2.4 g.
acid polymer: 0.1 g.
glycerol: 3.5 g.
water: 0.5 g.
adhesion—good, compression—good, residue—very good. Resistivity $9.3 \times 10^1$ ohm-cm.

EXAMPLE 14

Evanol (a polyvinyl alcohol, as additional thickener) registered trademark of E. I. DuPont de Nemours: 2.4 g.
acid polymer: 0.1 g.
glycerol: 3.5 g.
water: 0.5 g.
Resistivity $6.89 \times 10^3$ ohm-cm.

EXAMPLE 15

Polyvinylpyrollidone (as additional thickener): 2.5 g.
acid polymer: 1.5 g.
glycerol: 7 g.
water: 1 g.
adhesion—very good. Resistivity $3.32 \times 10^2$ ohm-cm.

EXAMPLE 16

Polyvinylpyrollidone (as additonal thickener): 3 g.
acid polymer: 1 g.
glycerol: 4 g.
methanol: 10 g.
water: 1 g.
adhesion—very good. Other properties—average.

EXAMPLE 17

Polyacrylamide-grafted corn starch (as additional thickener): 2 g.
acid polymer: 2 g.
water: 4 g.
glycerol: 4 g.
heat to 80° C. and press to sheet form. Resistivity $1.56 \times 10^4$ ohm-cm.

EXAMPLE 18

Polyvinylpyrrollidone (as additional thickener): 2 g.
acid polymer: 2 g.
water: 4 g.
glycerol: 4 g.
heat to 80° C. and press to sheet form. Resistivity $3.32 \times 10^2$ ohm-cm.

EXAMPLE 19

Evanol (a polyvinyl alcohol as additional thickener) registered trademark of E. I. DuPont de Nemours: 2 g.
acid polymer: 2 g.
water: 4 g.
glycerol: 4 g.
heat to 80° C. and press to sheet form. Resistivity $6.89 \times 10^3$ ohm-cm.

EXAMPLE 20

Xanthan gum (as additional thickener): 2 g.
acid polymer: 2 g.
water: 4 g.
glycerol: 4 g.
heat to 80° C. and press to sheet form. Resistivity $2.6 \times 10^2$ ohm-cm.

EXAMPLE 21

Hydroxypropyl guar (as additional thickener): 2 g.
acid polymer: 2 g.
water: 4 g.
glycerol: 4 g.
heat to 80° C. and press to sheet form. Resistivity 9.39×10$^1$ ohm-cm.

EXAMPLE 22

Xanthan gum: 10 g.
polymer salt (lithium carbonate salt): 2 g.
glycerol: 10 g.
water: 10 g.
heat to 80° C. and press to sheet form. Flexibility—acceptable, adhesion—acceptable, residue—acceptable, elasticity—acceptable, compression—acceptable.

EXAMPLE 23

Guar gum: 10 g.
polymer (lithium carbonate salt): 3 g.
glycerol: 10 g.
water: 10 g.
heat to 80° C. and press to sheet form. Flexibility—acceptable, adhesion—acceptable, residue—acceptable, elasticity—acceptable, compression—acceptable.

The Xanthan gum used herein was Galaxy XB Xanthan gum obtained from General Mills Chemicals as was the starch graft polymer used (SGP5025) and the hydroxypropyl guar used (HPG406). The Evanol was E. I. DuPont de Nemours and Co., grade 51-05 polyvinyl alcohol. The polyvinylpyrollidone was obtained from General Aniline and Film Corp., control No. 390.

Copolymers of the polymerized monomer may also be used as the conductive member 12. For example, copolymers have been successfully prepared with acrylamide, N-vinylpyrollidone and acrylic acid. Specific examples of copolymerization with acrylamide and with acrylic acid are as follows:

EXAMPLE 24

Preparation and polymerization same as in Example 1.
Acid monomer: 49.7 g.
acrylamide: 17.04 g.
water: 100 g.
potassium bisulfite (initiator): 2 ml of 0.38 g./100
potassium persulfate (initiator): 2 ml of 0.38 g./100 solution
ferrous Sulfate heptahydrate (initiator): 2 ml of 0.24 g./100 solution The resistance for a 1×1.5×0.125 inch sheet was 13 kilo-ohms.

EXAMPLE 25

Acid monomer: 25 g.
acrylic acid: 4 g.
water: 25 g.
potassium bisulfite (initiator): 1 ml of 0.38 g./100 solution
potassium persulfate (initiator): 1 ml of 0.38 g./100 solution
ferrous sulfate heptahydrate (initiator): 1 ml of 0.24 g./100 solution The resistance of a 1×1.5×0.125 inch sheet was 1.5 kilo-ohms.

In general, the preferred relative amounts of the constituents to be used in forming the skin contacting member 12 are indicated below, exclusive of any additional constituents.

|  | Amounts Ingredients % by weight | Range of Ingredients % by weight |
| --- | --- | --- |
| Polymer/water | about 50/50 | about 25-65/75-35 |
| polymer/alcohol | about 70/30 | about 30-70/70-30 |
| polymer/(water + alcohol in any proportion) | about 57/(39 + 4) | about 30-70/(water + alcohol in any proportion) = 70-30 |

It is important to understand that all of the polyamps polymers described above by way of Example exhibit high conductivity. However, the addition of soluble, ionizable metal salts such as KCl and NaCl has an additional benefit in the electrical properties of sensing or monitoring type electrodes. Chloride salts are particularly preferred. While it is generally accepted that salt addition to water soluble polymers improves conductivity, salt addition to the polymer improves conductivity only slightly, not on an order of tenfold. Nevertheless, it does provide unusually improved sensing properties as in EKG testing for example.

Following are examples of electrodes in which salt has been added. The same purging treatment and initiator were used as described above for Example 2. Thickness of the substrate material was about 0.100 inches.

EXAMPLE 26

89.3 grams of a 56% sodium salt solution of monomer were mixed with 7.7 grams of polyacrylic acid and 2.2 grams of 1% methylene-bis-acrylamide solution. To this solution, 1.0 grams of NaCl was added. The resultant polymerized product consisted of cross-linked polymer blended with polyacrylic acid and showed enhanced electrical conductivity properties. In sensing applications, decreased motion artifacts were noted i.e., less background noise as opposed to the same formulation without NaCl.

EXAMPLE 27

114 grams of a 56% sodium salt solution of monomer were mixed with 6 grams of glycerine and 2 milliliters of a 1% solution of methylene-bis-acrylamide. To this solution, 1 gram of NaCl was added. Again, the resultant polymerized product had enhanced properties as in Example 26 that were not present before the addition of NaCl.

The polyacrylic acid added to the adhesiveness of the material and the methylene-bis-acrylamide caused cross-linking of the polymer.

As can be seen from the examples provided herein, a wide variety of additives may be included in conductive member 12, it only being necessary that it include, in varying amounts, the essential polymer or copolymer of 2-acrylamido-2-methylpropanesulfonic acid or one of its soluble salts. Generally, any amount of polymer is satisfactory so long as a sufficient amount is included with water and/or alcohol to provide the requisite adhesive and flexible qualities. Various thicknesses may be used as desired and any electrode configuration with or without backing support and current distribution member may be used. As already pointed out above in one example, release paper of the waxed, silicone-treated or plastic coated variety may be included to protect the substrate prior to use.

Many changes and embodiments of the invention will become apparent to those of ordinary skill in this art without departing from the scope of the invention. The description herein is not intended to be limiting in any sense and the exclusive property rights claimed are defined hereinbelow.

We claim:

1. A method of preparing a conductive member for an electrode, the member containing as an essential component a polymer selected from the group consisting of 2-acrylamido-2-methylpropanesulfonic acid, its salts, copolymers of the acid, copolymers of the salts of the acid and mixtures thereof wherein the polymer component is formed simultaneously with the formation of the member.

2. A method of preparing conductive material for skin contacting electrodes comprising:
dissolving a polymerizable material selected from the group consisting of 2-acrylamido-2-methylpropanesulfonic acid, its salts and mixtures thereof in a solvent selected from the group consisting of water, alcohols and mixtures thereof, and
polymerizing the polymerizable material in the solvent to form the conductive material.

3. The method according to any of the preceding claims 1 or 2 wherein additional conductivity improving constituents are added to the components of the conductive member prior to its formation.

4. The method according to claim 3 wherein the conductivity improving constituents comprise soluble salts.

5. The method according to claim 4 wheren the salts are chlorides.

6. The method according to claim 5 wherein the salt is NaCl.

7. The method of preparing a medical electrode, comprising the steps:
providing a quantity of a material selected from the group consisting of 2-acrylamido-2-methylpropanesulfonic acid, its salts, copolymers of the acid, copolymers of the salts of the acid and mixtures thereof;
polymerizing the material to form a tacky conductive body, and
attaching electrical lead means to the body.

8. The method of claim 7 wherein the polymerization step is carried out in the presence of a solvent selected from the group consisting of water, an alcohol and mixtures thereof.

9. The method of claim 7 wherein the tacky conductive body is provided with a backing support.

10. The method of claim 7 wherein the polymerization step is carried out in the presence of additional conductive constituents.

11. The method of claim 7 wherein a current distribution member is attached to the tacky conductive body.

12. The method of claim 9 wherein the backing is attached to the current distribution member.

13. The method of preparing a medical electrode, comprising the steps:
forming a tacky conductive body including as an essential constituent thereof a quantity of polymeric material selected from the group consisting of 2-acrylamido-2-methylpropanesulfonic acid, its salts and copolymers of the acid, copolymers of the salts of the acid and mixtures thereof and a quantity of a solvent selected from the group consisting of water, an alcohol and mixtures thereof, and
attaching electrical lead means to the body.

14. The method of claim 13 wherein the polymeric material is formed during formation of the body.

15. The method of claim 13 wherein the polymeric material is pre-formed.

16. The method of either claim 7 or claim 13 wherein the formation of the body is by casting or molding.

* * * * *

UNITED STATES PATENT AND TRADEMARK OFFICE
CERTIFICATE OF CORRECTION

PATENT NO. : 4,581,821

DATED : April 15, 1986

INVENTOR(S) : Patrick T. Cahalan et al

It is certified that error appears in the above-identified patent and that said Letters Patent are hereby corrected as shown below:

Column 1, line 40, the word appearing as "prepare" should read --prepared--.

Column 2, line 4, "4b" should read --14b--.

Column 7, line 47, after the numeral "100" the word --solution-- should be added.

Signed and Sealed this

Twenty-second Day of July 1986

[SEAL]

Attest:

DONALD J. QUIGG

Attesting Officer

Commissioner of Patents and Trademarks